(12) United States Patent
Ehlert Taylor (10) Patent No.: US 11,607,850 B2
(45) Date of Patent: Mar. 21, 2023

(54) METHODS AND SYSTEMS FOR RENDERING THREE-DIMENSIONAL GAIT ACCELERATION PLOTS ON GRAPHICAL USER INTERFACES

(71) Applicant: OPTUM LABS, LLC, Minneapolis, MN (US)

(72) Inventor: Sara Ehlert Taylor, Cambridge, MA (US)

(73) Assignee: OPTUM LABS, LLC, Minneapolis, MN (US)

( * ) Notice: Subject to any disclaimer, the term of this patent is extended or adjusted under 35 U.S.C. 154(b) by 1015 days.

(21) Appl. No.: 16/250,196

(22) Filed: Jan. 17, 2019

(65) Prior Publication Data

US 2019/0143604 A1 May 16, 2019

Related U.S. Application Data

(62) Division of application No. 15/193,310, filed on Jun. 27, 2016, now Pat. No. 10,220,577.

(Continued)

(51) Int. Cl.
*B29C 64/386* (2017.01)
*G01P 15/18* (2013.01)
(Continued)

(52) U.S. Cl.
CPC .......... *B29C 64/386* (2017.08); *A61B 5/112* (2013.01); *A61B 5/74* (2013.01); *B29C 64/00* (2017.08);
(Continued)

(58) Field of Classification Search
CPC ....... B29C 64/386; A61B 5/112; G01P 15/18; G05B 2219/49007
See application file for complete search history.

(56) References Cited

U.S. PATENT DOCUMENTS

| | | | |
|---|---|---|---|
| 7,145,461 | B2 | 12/2006 | Lehrman et al. |
| 2010/0024531 | A1 | 2/2010 | Senoo |

(Continued)

FOREIGN PATENT DOCUMENTS

WO    WO 2015066718 A2    5/2015

OTHER PUBLICATIONS

Mitsuru Yoneyama, Visualizing Gait Symmetry/Asymmetry from Acceleration Data, Published Online: Nov. 25, 2013, Computer Methods in Biomechanics and Biomedical Engineering, vol. 18, No. 9, 2013 Taylor & Francis, pp. 923-930 (Year: 2013).*

(Continued)

*Primary Examiner* — Toan M Le
(74) *Attorney, Agent, or Firm* — Alston & Bird LLP (57) ABSTRACT

Embodiments represent acceleration along three orthogonal axes at two or more times as a three dimensional plot. Each point in the plot is positioned according to three coordinates, each of which is proportional to the amount of acceleration along one of the orthogonal axes at a moment in time. Some embodiments render the three dimensional plot as a three dimensional article of manufacture in which each point in the plot is represented by a volume of material. Some embodiments represent the three dimensional plot in two dimensions in a graphical interface. System embodiments may include an accelerometer, processor, output device, and a non-transitory computer readable medium storing instructions causing the processor to map points with coordinates proportional to acceleration along the respective axes to a virtual three-dimensional plot and then control the output device to render the plot in two or three dimensions.

18 Claims, 9 Drawing Sheets

Related U.S. Application Data (60) Provisional application No. 62/188,802, filed on Jul. 6, 2015.

(51) Int. Cl.

| | | |
|---|---|---|
| *G05B 19/4099* | (2006.01) | |
| *B33Y 50/02* | (2015.01) | |
| *A61B 5/11* | (2006.01) | |
| *B33Y 10/00* | (2015.01) | |
| *B33Y 30/00* | (2015.01) | |
| *B33Y 80/00* | (2015.01) | |
| *A61B 5/00* | (2006.01) | |
| *B29C 64/00* | (2017.01) | |

(52) U.S. Cl.
CPC .............. *B33Y 10/00* (2014.12); *B33Y 30/00* (2014.12); *B33Y 50/02* (2014.12); *B33Y 80/00* (2014.12); *G01P 15/18* (2013.01); *G05B 19/4099* (2013.01); *G05B 2219/49007* (2013.01)

(56) References Cited

U.S. PATENT DOCUMENTS

| | | |
|---|---|---|
| 2015/0142152 A1 | 5/2015 | Rezayat |
| 2015/0197064 A1 | 7/2015 | Walker et al. |
| 2015/0230734 A1 | 8/2015 | Cheung |
| 2015/0306823 A1 | 10/2015 | Askedall et al. |
| 2018/0001569 A1 | 1/2018 | Garcia et al. |
| 2018/0022029 A1 | 1/2018 | Morovic et al. |
| 2018/0032059 A1 | 2/2018 | Morovic et al. |

OTHER PUBLICATIONS

Abstractor Mitsuru Yoneyama, Nov. 25, 2013, 3 pp. (Year: 2013).*
"List of Physical Visualizations and Related Artifacts," Nov. 19, 2014, as retrieved from http://dataphys.org/list/3d-social-networks/.
Bouten, C.V.C et al., "Effects of placement and orientation of body-fixed accelerometers on the assessment of energy expenditure during walking," Medical & Biological Engineering & Computing, Jan. 1997, pp. 50-56, vol. 35.
Axelsson, Patrik and Mikael Norrlof, "Method to Estimate the Position and Orientation of a Triaxial Accelerometer Mounted to an Industrial Manipulator," 10th International IFAC Symposium on Robot Control, Dubrovnik, Croatia, 2012.
Botero, J.S., V.W. Hernandez, and E. Fernandez, "Orientation of a Triaxial Accelerometer using a Homogeneous Transformation matrix and Kalman Filters," International Journal of Smart Sensing and Intelligent Systems, vol. 7, No. 4, pp. 1631-1646, Dec. 2014.
Igoe, Tom, "Howto Locate (almost) Anything," Making Things Talk: Practical Methods for Connecting Physical Objects, O'Reilly, 2007, pp. 291-298.
NonFinal Office Action for U.S. Appl. No. 16/250,142, dated Oct. 14, 2022, (11 pages), United States Patent and Trademark Office, US.

* cited by examiner

METHODS AND SYSTEMS FOR RENDERING THREE-DIMENSIONAL GAIT ACCELERATION PLOTS ON GRAPHICAL USER INTERFACES

This application is a division of and claims the benefit of U.S. non-provisional application Ser. No. 15/193,310 which was filed on Jun. 27, 2016, the entire contents of which are herein incorporated by reference. Application Ser. No. 15/193,310, in turn, claimed benefit of provisional application 62/188,802 filed on Jul. 6, 2015, the entire contents of which were therein incorporated by reference.

FIELD OF THE INVENTION

The current disclosure relates to graphical user interfaces, methods, and systems for rendering three-dimensional gait acceleration plots in two dimensions.

BACKGROUND

Individuals move on foot in a variety of ways including walking, running, and ascending or descending stairs or sloped surfaces. Gait may be assessed in terms of a gait cycle, also called a stride. A stride begins when a reference foot (either the left or right) makes contact with the ground and ends when it next contacts the ground. A stride is composed of two steps. A step is the action occurring in the interval from the moment that one foot contacts the ground to the moment when the other foot contacts the ground. A step may be attributed to either the left foot or the right foot, though actions of both feet are necessary to take a step.

Gait analysis has been used not only to document gait abnormalities but also to determine the underlying causes of the abnormalities and, in some cases, to select treatment. Instruments used in conventional gait analysis laboratories detect a variety of measures associated with walking. Some measure the position of the body and limbs while others measure the forces resulting from walking or muscle activation involved in walking. However, these conventional gait analysis instruments may be expensive and cumbersome and may only measure a subject's gait in the laboratory and not during activities of daily living.

Over the past decade, accelerometers have become smaller, less expensive, more accurate, and more energy efficient. An accelerometer may refer to a device that measures either linear or angular acceleration. However, accelerometers measuring angular acceleration may also be referred to as gyroscopes, gyrometers, or gyros. An accelerometer may also refer to a device that measures acceleration in more than one direction. Three-axis (triaxial) accelerometers in which the axes are at least approximately orthogonal to one another are now a common feature in devices ranging from smartphones to fitness trackers.

Fitness trackers may estimate quantities of physical activity such as step count, calories burned, or distance traveled. However, such quantitative measures provide little information about gait quality. Viewing acceleration data as a signal (in which the x-axis represents time and the y-axis represents the quantity of acceleration) may provide some insight as to gait quality. For signal graphs however, viewers may find it difficult to compare the acceleration data from one step to that of another. Comparing steps in a signal graph requires the viewer to determine boundaries between steps and mentally superimpose the acceleration signal of one step over that of another. Such divisions and superimpositions are mentally taxing. Viewing acceleration signals from multiple axes further compounds the effort required to compare one step to another.

Figure 1:
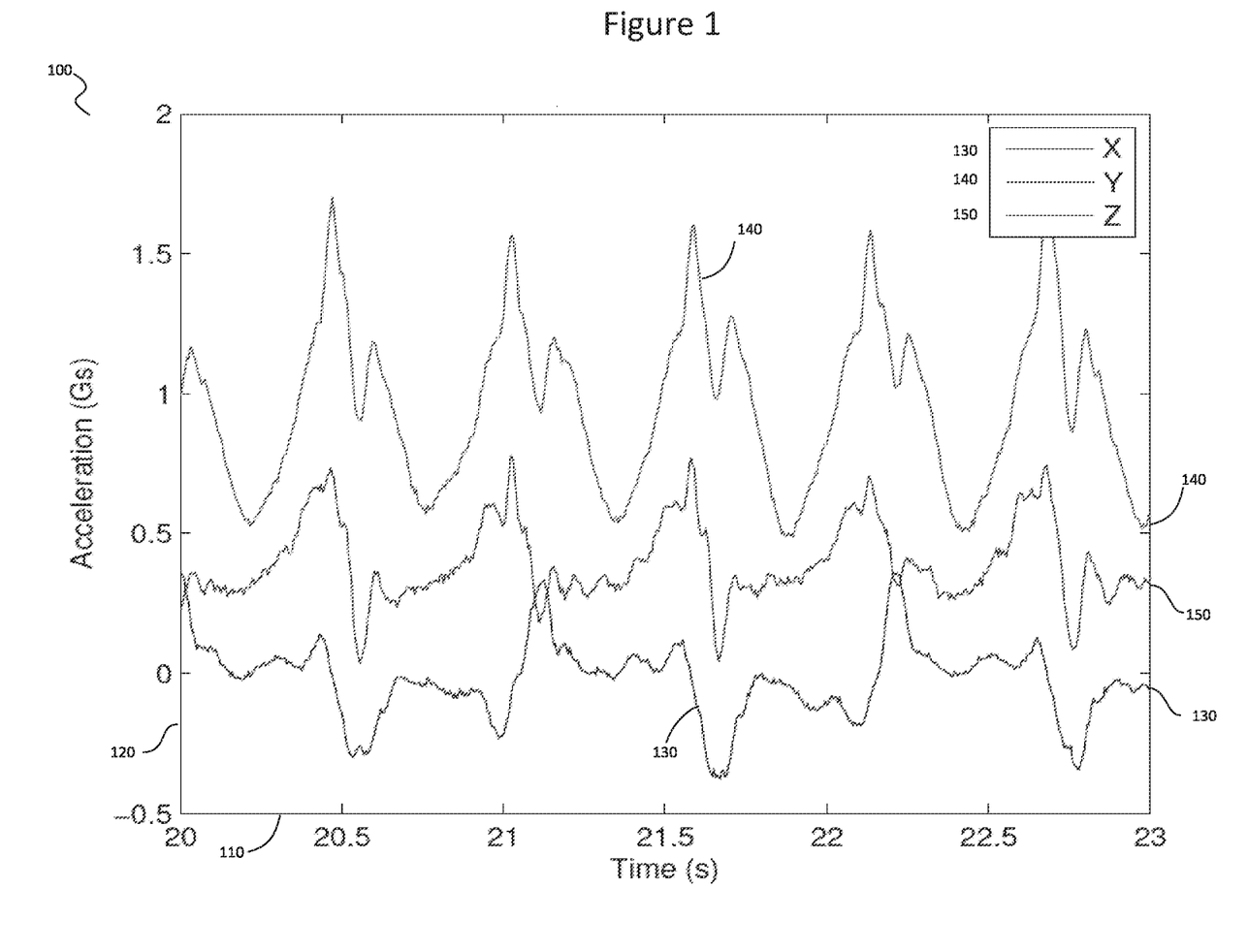
FIG. 1 presents a graph showing three accelerometer signals representing acceleration along three orthogonal axes of a triaxial accelerometer coupled to an individual taking steps.

FIG. 1 presents a graph (100) showing three signals representing acceleration along three orthogonal axes of a triaxial accelerometer coupled to an individual taking steps. The graph's horizontal axis (110) represents time in seconds and the graph's vertical axis (120) represents acceleration in g (freefall acceleration in Earth's gravity). Acceleration along the accelerometer's x axis is represented by the bottommost line (130) of the graph (100). Acceleration along the accelerometer's y axis is represented by the topmost line (140) of the graph (100). Acceleration along the accelerometer's z axis is represented by line 150 on the graph (100) which, generally, lies between the other two lines.

Additive manufacturing (also called "three dimensional printing" or "3D printing") encompasses a variety of techniques used to manufacture objects in three-dimensions using automated, computer-controlled processes. In some types of additive manufacturing, a three dimensional printer (also referred to as an additive manufacturing device) deposits a series of layers. Each layer has a specified shape composed of small, point-like deposits, each of which is placed on a plane according to two coordinates. The deposits forming each layer adhere to the deposits of the layer below it. The number of layers and/or height of each layer effectively act as a third coordinate allowing for the placement of the point-like deposits at precise positions in space. Additive manufacturing may be used to fabricate objects from a variety of materials.

SUMMARY

Embodiments may represent acceleration along three orthogonal axes at two or more times as a three dimensional plot. Each point in the plot may be positioned according to three coordinates, each of which is proportional to the amount of acceleration along one of the orthogonal axes at a moment in time. Some embodiments render the three dimensional plot as a three dimensional article of manufacture in which each point in the plot is represented by a volume of material. Method embodiments include the use of additive manufacturing techniques to fabricate such an article of manufacture. Some embodiments represent the three dimensional plot in two dimensions in a graphical interface using techniques of visual perspective to create the impression of a third dimension. System embodiments comprise an accelerometer, processor, output device, and a non-transitory computer readable medium storing instructions causing the processor to map points with coordinates proportional to acceleration along the respective axes to a virtual three-dimensional plot and then direct the output device to render the plot in two or three dimensions.

BRIEF DESCRIPTION OF THE DRAWINGS

FIG. 4 presents eight perspectives of a manufacture representing a plot of acceleration data along three axes for a gait cycle of a third individual according to certain embodiments of the present disclosure.

DETAILED DESCRIPTION

Embodiments described herein represent acceleration along three orthogonal axes at two or more times as a three dimensional plot. Each point in the plot may be positioned according to three coordinates, each of which is proportional to the amount of acceleration along one of the orthogonal axes at a first moment in time. Each point in the plot may be coupled, either physically or visually, to at least an adjacent point. The adjacent point is positioned according to coordinates proportional to acceleration readings along the three orthogonal axes at a second time. Except for the first and last points in the plot, each point is coupled to two adjacent points, one of which may be positioned according to acceleration at the next previously sampled time and the other positioned according to the next subsequently sampled time.

Because none of the axes of the plot represents time, the plot may be viewed as being time-independent. To the extent that similar acceleration patterns occur from one stride to the next, the patterns may align irrespective of step duration. Using this time-independent representation, there is no need to choose arbitrary boundaries between the steps. Additionally, there is no need to scale the duration of one step so that its acceleration patterns align with those of another. If the accelerometer generates acceleration readings at a fixed frequency, slower movements shown in a time-independent plot will manifest as points that are more densely clustered and vice versa.

Embodiments may include a solid, three dimensional manufacture comprising a model of the three dimensional plot. The points in the plot may not be true geometric points with zero dimension but are representative of such points and may be composed of some volume of material. In some embodiments, the points are close enough to one another relative to the size of the material representing each point that the pieces of material representing the points touch or overlap one another. In some embodiments, the points are far enough from one another relative to the size of the material representing each point that the pieces of material representing the points do not touch or overlap one another and may be connected by some volume of material in a shape representing a line segment or curve.

Figure 2:
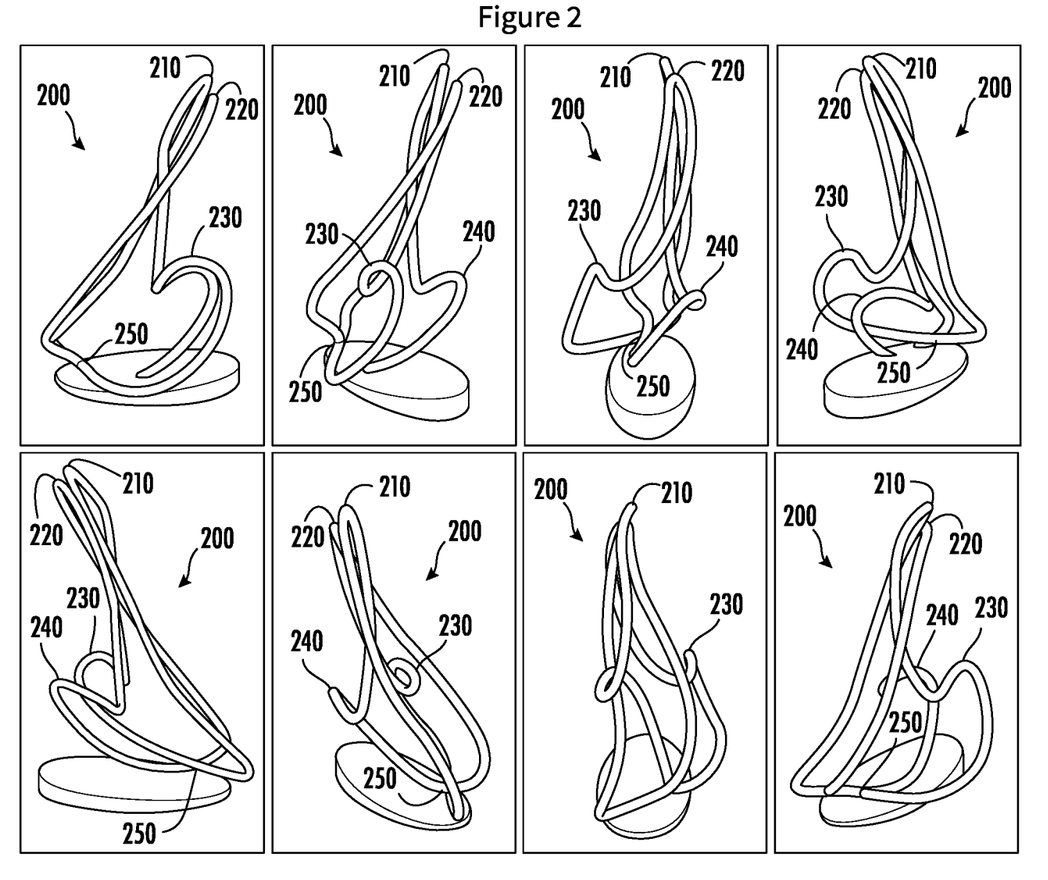
FIG. 2 presents eight perspectives of a manufacture representing a plot of acceleration data along three axes for a gait cycle of a first individual according to certain embodiments of the present disclosure.
Figure 3A:
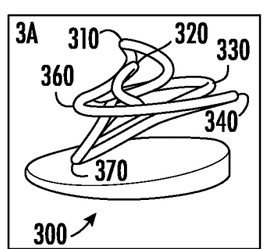
FIG. 3 presents eight perspectives of a manufacture representing a plot of acceleration data along three axes for a gait cycle of a second individual according to certain embodiments of the present disclosure.
Figure 3B:
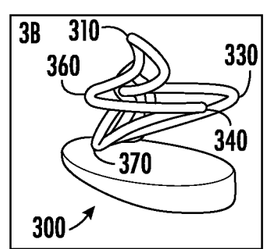
Figure 3C:
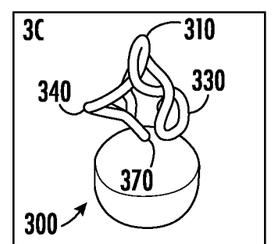
Figure 3D:
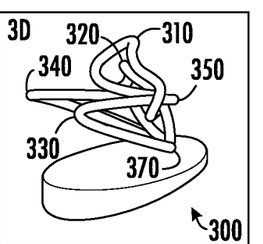
Figure 3E:
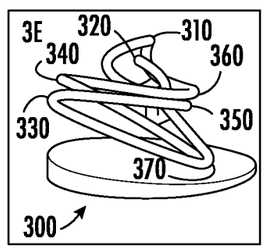
Figure 3F:
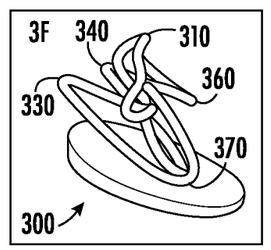
Figure 3G:
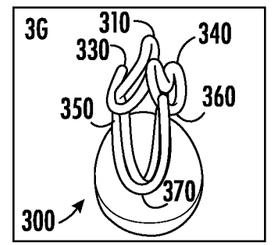
Figure 3H:
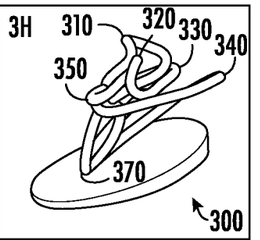

FIGS. 2-4 each present eight perspectives of an article of manufacture (a "manufacture") each of which comprises a three dimensional plot representing acceleration data along three axes during a single gait cycle. Each plot represents gait acceleration data taken from a different individual. The volumes of material representing each acceleration point are large enough relative to the distance between the points they represent that distinct points are not visible in these manufactures. If gait cycles of an individual are sufficiently similar, successive gait cycles should trace approximately the same path through the three dimensional plot for each gait cycle. Thus, each of the gait cycles rendered in these manufactures appear as a continuous loop without distinct starting or ending points.

FIG. 2 presents eight perspectives (2A-2H) of a manufacture (200) comprising a three dimensional plot representing gait acceleration of a first individual. The plot suggests an approximate symmetry between points 210 and 220 and between upward curves 230 and 240. Points 210 and 220 both represent times of rapid change in acceleration as indicated by their sharp curvature. Point 210 is the topmost point of the plot and represents the point in the gait cycle with maximum acceleration in the vertical direction. Point 220 represents a local maximum in the Y direction and is only slightly lower than point 210. Curve 230 contains the forward-most and right-most points of the plot indicating maxima of forward and lateral acceleration, respectively. Curve 230 corresponds approximately with curve 240, though curve 240 does not extend as far forward or as far to the side as curve 230. From some perspectives such as 2F and 2G, curves 230 and 240 appear to show rapid changes in acceleration, but perspectives such as 2A and 2D show a more gradual change in acceleration. The acceleration lines cross over one another, effectively occupying the same space, at point 250 (visible from some perspectives). Perspectives such as 2C and 2G demonstrate that, while acceleration during the gait cycle may be approximately symmetric, it is not perfectly so and asymmetries in the acceleration plot may be indicative of gait asymmetries.

FIG. 3 presents eight perspectives (3A-3H) of a manufacture (300) comprising a three dimensional plot representing gait acceleration of a second individual. Seven points of rapid change in acceleration are labeled. The plot suggests an approximate symmetry between points 310 and 320, between points 330 and 340, and between points 350 and 360. Points 310 and 320 are each local maxima in the vertical direction with 310 being the top-most point in the plot and higher than 320. Points 330 and 340 are the points farthest in the forward direction (towards the higher side of the base). Points 350 and 360 are the points farthest in the backward direction (towards the lower end of the base) except for point 370. Point 370 is both the lowest and back-most point of the plot and a point at which two strands of the loop intersect. Each of the numbered points shows a rapid change in acceleration.

FIG. 4 presents eight perspectives (4A-4H) of a manufacture (400) comprising a three dimensional plot representing gait acceleration of a third individual. The plot of FIG. 4 is generally characterized by gradual curves as opposed to the sharp changes in acceleration that characterized the plot of FIG. 3. Five areas of curvature have been labeled. Area 410 is the area of sharpest curvature, is an area where the plot overlaps itself, and is near to the highest and front-most point of the plot. The plot suggests an approximate symmetry between areas 420 and 430 and between areas 440 and 450. Areas 420 and 430 both inflect downwards relative to area 410. Areas 440 and 450 are near both the lowest points of the plot and the rear-most points of the plot and turn back towards area 410.

The manufactures shown in FIGS. 2-4 allow a user to intuitively distinguish the gait of one individual from another. A step cycle plot may be viewed as an accelerometric signature of an individual. An individual may have a recognizable signature even though no two signatures, or steps, from that individual are identical. The manufacture pictured in FIG. 2 is much taller than the other two indicating a much greater vertical component to the gait of the individual whose acceleration is represented. The gait represented by the model shown in FIG. 3 is longer front to back than its height indicating a high ratio of horizontal to vertical movement for that individual's gait. Additionally, the model in FIG. 3 possesses sudden changes in direction indicating that acceleration across all axes changed rapidly during the gait cycle. In contrast, the model pictured in FIG. 4 is characterized by generally gradual curves indicating that the gait represented by the model was generally free of rapid changes in acceleration. Similarly, the model pictured in FIG. 2 is characterized by generally gradual curves with the exceptions of points 210 and 220. Each of the plots exhibits an approximate symmetry, but none is perfectly symmetric. Asymmetries in acceleration my be indicative of asymmetries in leg anatomy or leg strength which may have diagnostic and other clinical applications. Notably, differences among the gait acceleration data in the three models may be understood intuitively as a product of this method of presentation. Applications for such manufactures include pedagogy to foster an intuitive understanding among students of the acceleration experienced during the gait cycle and of the differences in gait acceleration among individuals.

Models of three dimensional plots may be composed of a variety of materials and be fabricated using a variety of techniques. Some method embodiments use additive manufacturing devices and techniques to precisely position material representing each point of an acceleration plot in space and couple the material to material representing adjacent points.

Figure 5:
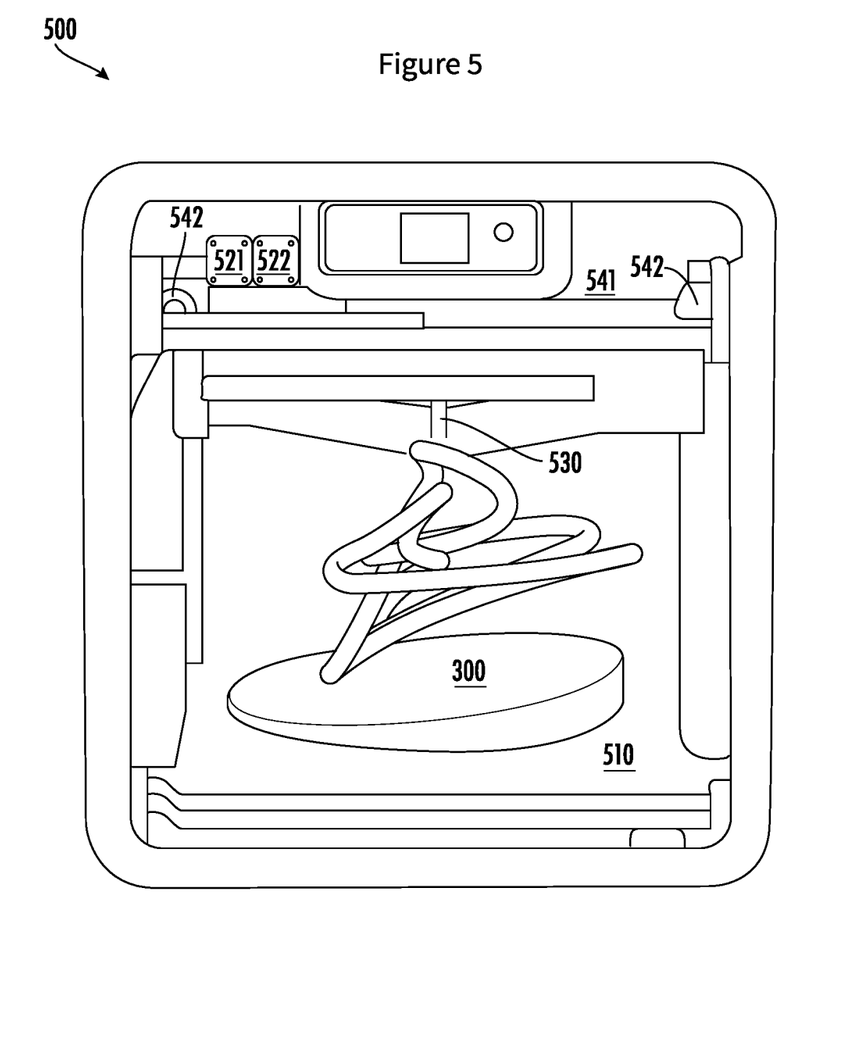
FIG. 5 illustrates an additive manufacturing device (three dimensional printer) producing a manufacture representing a plot of acceleration data along three axes for a gait cycle of an individual according to certain embodiments of the present disclosure.

FIG. 5 illustrates the manufacture shown in FIG. 3 (300) in an additive manufacturing device (500) capable of fabricating such a manufacture. The manufacture (300) rests on a platform (510) upon which layers of thermoplastic material may be deposited by at least one of two extruders (521, 522). The platform (510) is lowered and raised by turning threaded axle (530) effectively controlling the distance between the platform (510) and extruders (521, 522). (Axle 530 is sporadically visible in the background behind manufacture 300.) The side-to-side position of the extruders (521, 522) is controlled by a belt (541) stretched between two rollers (542). The front-to-back position of the extruders (521, 522) is controlled by a similar belt assembly (not visible). The platform (510) starts in its highest position, immediately next to the extruders (521, 522). The extruders (521, 522) melt small volumes of thermoplastic material and deposit them at specified x-y coordinates on the platform (510) where they cool and harden. This first layer of deposits is the first layer of manufacture (300). The platform (510) is then lowered by approximately the thickness of the thermoplastic deposits and the extruders (521, 522) deposit another layer of thermoplastic material on top of the first, again at specified x-y coordinates positioned by the belt assemblies (541, 542). The additive manufacturing device (500) adds successive layers in this fashion until the manufacture (300) is complete.

Overhangs—portions of the manufacture that do not rest on a lower layer or the platform (510)—present a technical challenge to creating manufactures fabricated using three dimensional printers. Some embodiments of the method support overhangs of the manufacture (300) with a support base made from a soluble material that does not become part of the final manufacture (300). In some embodiments, volumes of the soluble support base are deposited by one of the extruders (e.g. 521) while volumes of the non-soluble material forming the manufacture (300) are deposited by the other extruder (e.g. 522). At a specified height, the extruder depositing non-soluble material (e.g. 521) deposits the first layer of the overhang on top of the soluble base that has been built up, layer on layer, by the other extruder (e.g. 522). After the three dimensional printer (500) has completed the topmost layer of the manufacture (300), the resulting structure may be exposed to a solvent that dissolves the soluble support structure leaving an overhang that is now coupled to and supported by the non-soluble structure.

Some embodiments represent three-dimensional step plots on a two dimensional surface such as a display monitor, printed page, or surface such as a projection screen or wall upon which the image is projected. Such two-dimensional representations may use techniques of perspective to create the impression of three dimensions on a two-dimensional surface. Some embodiments show a series of perspective drawings animating the 3D plot and creating the impression that the 3D plot is changing orientation.

Figure 6:
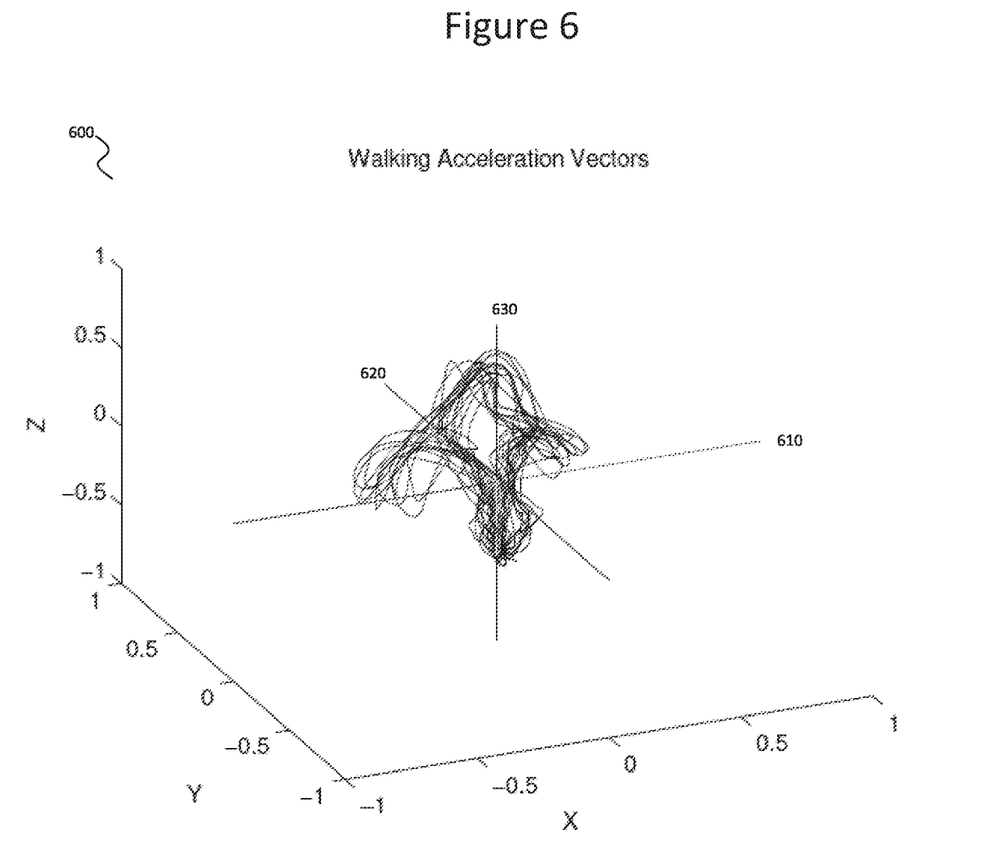
FIG. 6 presents a two-dimensional rendering of a three dimensional plot representing acceleration along three orthogonal axes during multiple walking steps according to certain embodiments of the present disclosure.
Figure 7:
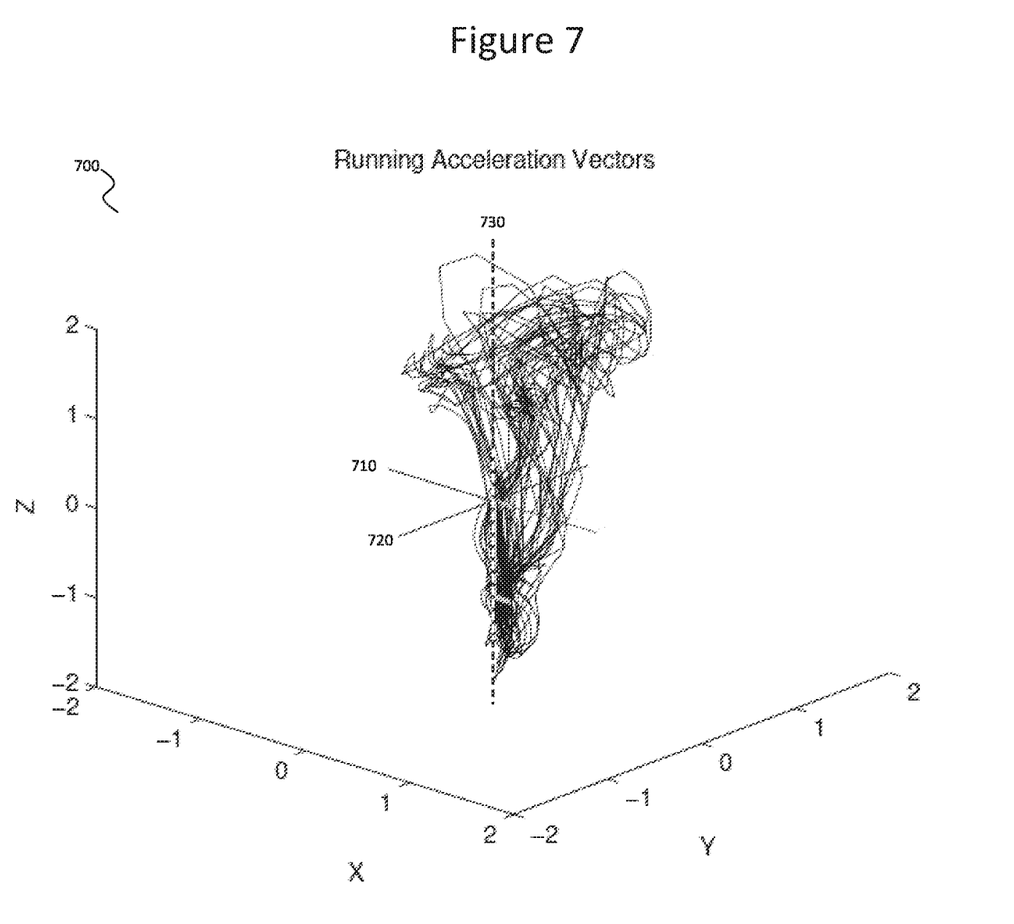
FIG. 7 presents a two-dimensional rendering of a three dimensional plot representing acceleration along three orthogonal axes during multiple running steps according to certain embodiments of the present disclosure.

FIGS. 6 and 7 each present a three-dimensional acceleration plot rendered on a two-dimensional surface. FIG. 6 presents a plot (600) of accelerometer data for a number of steps taken while a user was walking. The origin lines for the x, y, and z axes are represented by line segments 610, 620, and 630, respectively. The range for each of the axes extends from −1 g to 1 g. FIG. 7 presents a plot (700) of accelerometer data for a number of steps taken while the user was running. The origin lines for the x, y, and z axes are represented by line segments 710, 720, and 730, respectively. Line segment 730 is dashed to contrast its background. The range for each of the axes extends from −2 g to 2 g.

Differences between the acceleration patterns of walking and running become readily apparent when plotted as in FIGS. 6 and 7. The magnitude of the running steps tends to be greater than that of the walking steps. (Note that the scale on the walking plot runs from 1 to −1 while the scale on the running plot runs from 2 to −2.) Additionally, there is more variability among the running steps than there is among the walking steps. A third difference is that the vertical (z) component of the running plot (700) has a much greater magnitude than accelerations in the x or y directions while accelerations among the three axes appear more evenly distributed in the walking plot (600). The presentation of gait accelerometer data in three dimensional plots such as 600 and 700 allow the viewer to identify differences in a visually intuitive manner that may also be identified by various statistical and machine learning algorithms.

Some embodiments analyze accelerometer data corresponding to steps taken by a user wearing the accelerometer and, based at least in part on the analysis, identify a characteristic of the user. Characteristics of the user may include, for example, the type of step activity (walking, running, climbing stairs, etc.), disease state, degree of health, diagnoses, location, or the identity of the user.

In order to assess the user's steps, a number of technical challenges emerge. One such challenge is to determine how the accelerometer is oriented relative to its surroundings and relative to the user to which it is attached. If the accelerometer is attached to the user in a particular orientation, the orientation of the accelerometer to its surroundings may be inferred. For example, if the accelerometer is clipped to the shirt-front of a user and the user is standing and walking in an upright position, one may infer that the z-axis is approximately vertical and approximately parallel to the user's anteroposterior axis. Correspondingly, the other two axes should be approximately parallel to the user's dorsoventral and lateral axes. However, such inferences are prone to error. Clothing can shift, the attachment to the clothing can slip, and the user may bend forward or backward or otherwise move in a position that is not perfectly upright. Such sources of error invite better methods of orienting accelerometers with multiple axes.

Gravity acts as a constant acceleration in one direction. The force of gravity may serve to orient acceleration readings relative to physical surroundings. Some embodiments having triaxial accelerometers use algorithms that process acceleration readings to determine the direction of gravity relative to three accelerometer axes. Of those embodiments, some may further calculate the amount of acceleration in the direction of gravity.

In some embodiments, a computer reorients acceleration vectors so that one component of each reoriented acceleration vector is in the direction of gravitational pull. The computer's processor receives readings from a triaxial accelerometer. Each of the readings corresponds to an acceleration vector having three components. Each of the three components represents a quantity of acceleration along one of three orthogonal axes (x, y, and z). The computer determines a non-zero acceleration vector (u) using readings generated when the accelerometer is at rest and determines $\hat{x}$ which is the unit vector in the positive x axis direction. The computer then virtually rotates the components of one or more readings about the z axis into the yz plane by calculating the cross product of u and g (Earth's gravity reference) to yield n, calculating the sine of angle n$\hat{x}$ using the cross product of n and $\hat{x}$, calculating the cosine of angle n$\hat{x}$ using the dot product of n and $\hat{x}$, and constructing a rotation matrix $R_z$ using the sine of angle n$\hat{x}$ and the cosine of angle n$\hat{x}$. Then, the computer virtually rotates the components of the one or more readings about the x axis by calculating the sine of angle ug using the cross product of u and g, calculating the cosine of angle ug using the dot product of u and g, and constructing a rotation matrix $R_x$ using the sine of angle ug and the cosine of angle ug. Finally, the computer multiplies components of the one or more readings by the inverse of $R_z$ to reverse the original rotation operation. Using method embodiments such as those described above, several acceleration vectors may be rotated in one calculation, assuming they share the same nonzero acceleration vector (i.e. the same gravity vector with respect to the device), thus greatly reducing needed calculation time.

In some circumstances, it may be useful to know the orientation of the accelerometer axes relative to the user wearing the accelerometer. Some embodiments use algorithms to determine the orientation of the three axes relative to the user's anteroposterior, dorsoventral, and lateral axes. The user's dorsoventral axis, lateral axis, anteroposterior axis, and the axis parallel to the force of gravity are referred to herein, collectively, as adjusted axes. Some embodiments use algorithms to calculate the amount of acceleration in the direction of one or more of the adjusted axes based at least in part on acceleration readings from three orthogonal accelerometer axes.

While the force of gravity may be useful to determine the accelerometer's orientation, it may also obscure acceleration caused by physical activity. Thus, some embodiments use algorithms to remove the portion of acceleration caused by gravity from one or more accelerometer axes or adjusted axes.

Some embodiments compare sets of accelerometer data collected during individual steps to one another as at least part of determining a characteristic of the user. Steps, however, may vary in their duration. Thus, some embodiments scale the duration of one or more steps to match the duration of a second step or other fixed period of time. Because each foot may generate acceleration patterns that are distinct from the other, some embodiments compare strides. A stride is a series of two contiguous steps, one made by the right foot and one made by the left.

Some embodiments analyze accelerometer data in the frequency domain. For example, some embodiments may use one or more Fourier transforms to break an acceleration signal into a number of component frequencies. The amplitude of each of the component frequencies, in comparison to the amplitudes of the other component frequencies, may indicate the relative importance of a particular frequency. A graph showing the amplitudes of the frequency components of a signal may be referred to as a frequency spectrum. Some embodiments use frequency spectra as indicators of the characteristic of the user. Embodiments may use various filters to reduce noise in the data. For example, some embodiments may use one or more low pass filters to remove aberrant high frequency noise.

Accelerometer data may also be used to estimate the movement and location of the user. Velocity may be represented as the integral of acceleration and position may be represented as the integral of velocity. Given that accelerometers generate discrete data readings, the Riemann sum of the accelerometer readings yields an approximation of the user's velocity in the direction in which acceleration is measured. For accelerometers with multiple axes, the user's velocity in each of the axis directions may be approximated. In one embodiment, a two-axis accelerometer is attached to a user with one of the axes approximately parallel to the user's dorsoventral axis and a second axis approximately parallel to the user's lateral axis. The user's position walking on a flat surface may then be estimated using a double Riemann sum of the acceleration readings in each directions. The previous embodiment is limited in that it may work best if the user stays in the same orientation without pivoting. A second embodiment accounts for user pivots by adding a gyrometer that measures angular acceleration around either the user's anteroposterior axis or an axis parallel to the force of gravity. (If the user is standing upright, the user's anteroposterior axis would be expected to be approximately parallel to the force of gravity.) A third embodiment adds a third linear axis orthogonal to the other two axes to estimate the user's velocity in the vertical direction. Yet another embodiment uses a triaxial accelerometer measuring linear acceleration along three orthogonal axes and angular acceleration around each of the axes to account for tilt.

When combined with information about the user's starting position, information about the user's velocity can be used to estimate the user's location. Multiplying the user's velocity by the time the user was at a particular velocity yields a distance in a particular direction. As discussed above, distance traveled may be calculated on one or more axes and input of angular acceleration may be used to account for tilt. Estimated distance traveled along two or more orthogonal axes may be used to calculate the user's position relative to a starting point.

Methods such as those described above may be performed by a system. Systems may include an accelerometer measuring acceleration along one or more axes. The acceleration measured may be linear or angular. Accelerometers measuring angular acceleration may also be referred to as gyroscopes, gyrometers, or gyros. Some accelerometers may additionally contain a magnetometer that orients acceleration readings relative to a magnetic field such as Earth's magnetic field. A so-called "9-axis accelerometer" contains a tri-axial accelerometer measuring linear acceleration along three orthogonal axes, angular acceleration around each of the orthogonal axes, and orientation relative to a magnetic field. A 9-axis accelerometer may also be referred to as an inertial measurement unit (IMU). The accelerometer may be attached to a user to measure the user's gait acceleration and may be housed in a portable device.

The accelerometer may be communicatively coupled to a processor. The processor may include one or more processing units (i.e. processors communicatively coupled to one another). The processor may be communicatively coupled to and execute instructions stored on a computer readable data storage (CRDS) (also referred to herein as a non-transitory computer-readable medium). The instructions may cause the processor to, for example, render a three dimensional plot of gait acceleration or identify a characteristic of the user. The CRDS may also store information from the accelerometer and processor outputs as it executes the instructions stored on the CRDS and/or processes stored readings from the accelerometer. Embodiments of the CRDS may include random access memory (RAM) and various types of non-volatile memory including, but not limited to, read-only memory (ROM), programmable read-only memory (PROM), erasable programmable read-only memory (EPROM), and/or electrically erasable programmable read-only memory (EEPROM). Embodiments of the CRDS may include magnetic storage (such as hard drives, floppy disks, and magnetic tape) and/or optical storage (such as CDs and DVDs).

Systems may also include an output device for presenting three dimensional acceleration plots or communicating the characteristic of the user. Output devices for presenting a three dimensional plot may include a three dimensional printer for fabricating a manufacture comprising a representation of a three dimensional plot. Three dimensional plots may also be presented in two dimensions on output devices including a display monitor, an image projector, or a printer for printing images on a page. Output devices for communicating a characteristic of a user may include, for example, a display monitor, image projector, printer, audio speaker, or tactile output. Output devices may include means for communicating with other devices or networks. For example, output devices may include various types of electromagnetic transmitters or receivers. Some embodiments may comprise input devices such as key pads or touch screens on which the user may enter information related to gait acceleration data or instructions influencing outputs.

For embodiments requiring time measurement, there are a number of potential time-measuring means. If the accelerometer generates readings at regular time intervals, the number of accelerometer readings may be used to measure the passage of time. Processors typically perform calculations on a regular time cycle and thus present another means for measuring time. Alternatively, a separate time-measuring device may be used. Examples of alternative time measuring devices include electric clocks such as quartz clocks, synchronous clocks, and radio-controlled clocks that are wirelessly synchronized with a time standard such as an atomic clock.

System components such as those described above may require a source of electrical power. Possible sources include various types of batteries as well as devices that collect ambient energy such as sunlight (e.g. photo-voltaic cells), body heat, and body motion. Components of a system that do not need to be mobile may use power from a commercial grid.

Components of the system may be communicatively coupled to other components. The processor, for instance, may receive information from the accelerometer, send information and/or instructions to the output device, and both send and receive information from the CRDS. These communications may be made with or without physical connections such as wires. Any of the communications may be accomplished wirelessly using signal types including radio and infrared. Common wireless communication protocols include Bluetooth (IEEE 802.15), Wi-Fi (IEEE 802.11), cellular communication protocols, and infrared data association protocols. Embodiments using wireless communications may include components such as transmitters and receivers. Systems may also communicate with other devices or networks, for example a personal computer or the Internet. In some embodiments, the user receives and/or sends information from the device through an Internet web site instead of or in addition to a user interface.

Figure 8:
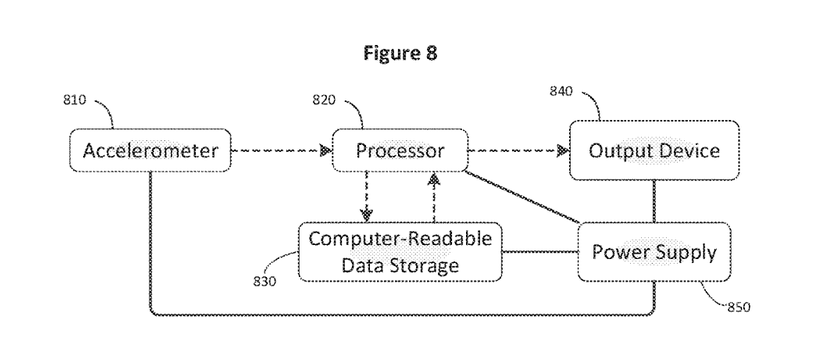
FIG. 8 presents a schematic diagram representing a system for measuring acceleration, according to certain embodiments of the present disclosure.

FIG. 8 presents a schematic diagram illustrating a system for processing acceleration data, according to certain embodiments of the present disclosure. The accelerometer (810) transmits unprocessed acceleration data to the processor (820). The dashed line connecting the two components indicates that information may be transferred, but does not necessarily require a physical connection. The processor (820) stores at least some of the acceleration data (in either unprocessed or processed form) on the CRDS (830). The processor (820) retrieves data from the CRDS (830) and processes it to render a three dimensional acceleration plot and/or determine a characteristic of the user. The processor (820) then communicates information such as a three dimensional plot of acceleration data or a characteristic of the user to an output device (840). The components listed above may be powered by a power supply (850). While this diagram shows a single power supply powering each of the components, system embodiments may use multiple power sources. Any configuration of power sources may be used so long as each component receives power, either directly from a power supply or indirectly through other components.

Figure 9:
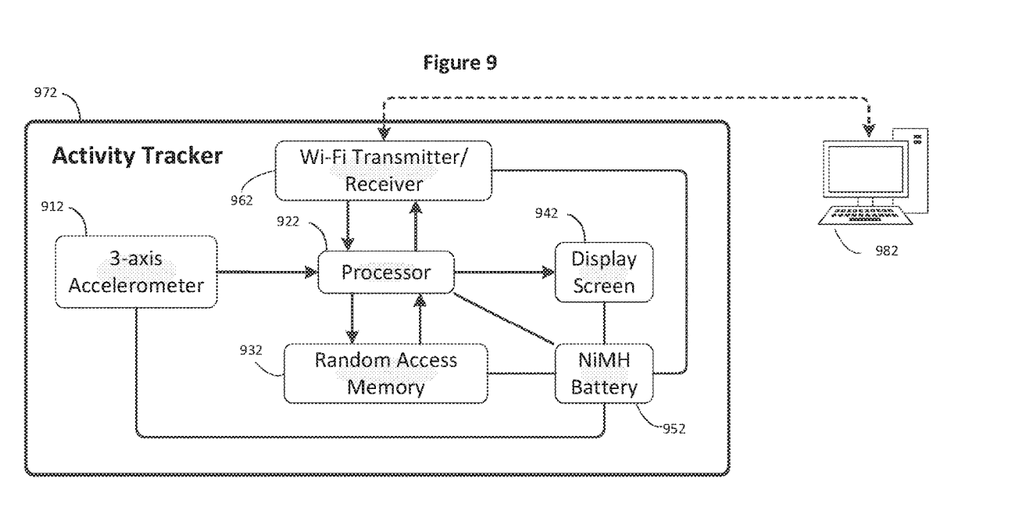
FIG. 9 presents a schematic diagram representing a system housed in a single device for measuring acceleration according to certain embodiments of the present disclosure.

FIG. 9 presents a schematic diagram illustrating an embodiment of the system in a portable, self-contained activity tracker (972) according to certain embodiments of the present disclosure. The rectangle surrounding the components indicates that they are all housed in the same device. The activity tracker (972) contains a 3-axis accelerometer (912), a processor (922), random access memory (932), a small display screen (942) visible from the outside of the device, and a rechargeable nickel metal hydride (NiMH) battery (952). The processor (922) performs the required calculations on the acceleration data and stores any necessary information on the RAM (932). The display (942) may communicate, among other information, a characteristic of the user. From time to time, the activity tracker (972) communicates with a second device (982) using radio signals. The activity tracker (972) contains a Wi-Fi transmitter-receiver (962) that exchanges data with the external device (982). This wireless communication may serve to communicate unprocessed or derived gait acceleration data to external devices (982), including those connected to the Internet.

Figure 10:
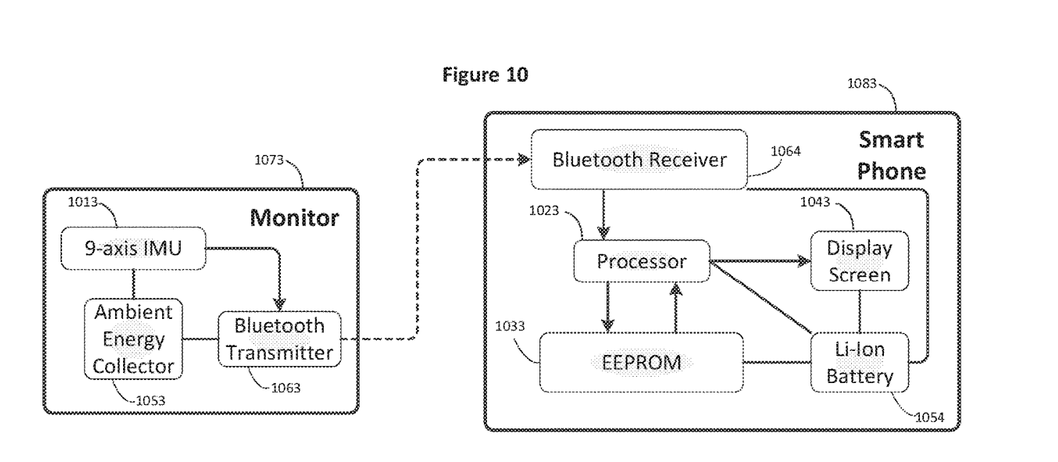
FIG. 10 presents a schematic diagram representing a system for measuring acceleration comprising a monitor device and separate smart phone according to certain embodiments of the present disclosure.

FIG. 10 presents a schematic diagram illustrating an embodiment in which a motion monitor (1073) wirelessly communicates acceleration data to an external device (1083) for processing, according to certain embodiments of the present disclosure. In this embodiment, the external device is a smartphone (1083). The motion monitor (1073) contains a 9-axis accelerometer/IMU (1013), a Bluetooth transmitter (1063), and an ambient energy collector (1053) to power the other two components. The ambient energy collector may, for example, include a photovoltaic cell for capturing light energy. The Bluetooth transmitter (1063) transmits raw (unprocessed) accelerometer data to a Bluetooth receiver (1064) in the smartphone (1083). The Bluetooth receiver (1064) then relays the raw acceleration data to the processor (1023) which, in turn, stores and retrieves acceleration data from the electronically erasable programmable read only memory (EEPROM) (1033). The processor (1023) may render a depiction of a three dimensional acceleration plot or communicate a characteristic of the user via the display screen (1043) on the smartphone (1083). All the components in the smartphone (1083) are powered by a lithium ion (Li-Ion) battery (1054). The smartphone (1083) may, optionally, communicate raw or processed acceleration data to other external devices via cellular frequencies and data protocols. The smartphone (1083) may also, optionally, be used as an input device into which a user could enter data related to gait acceleration data.

Figure 11:
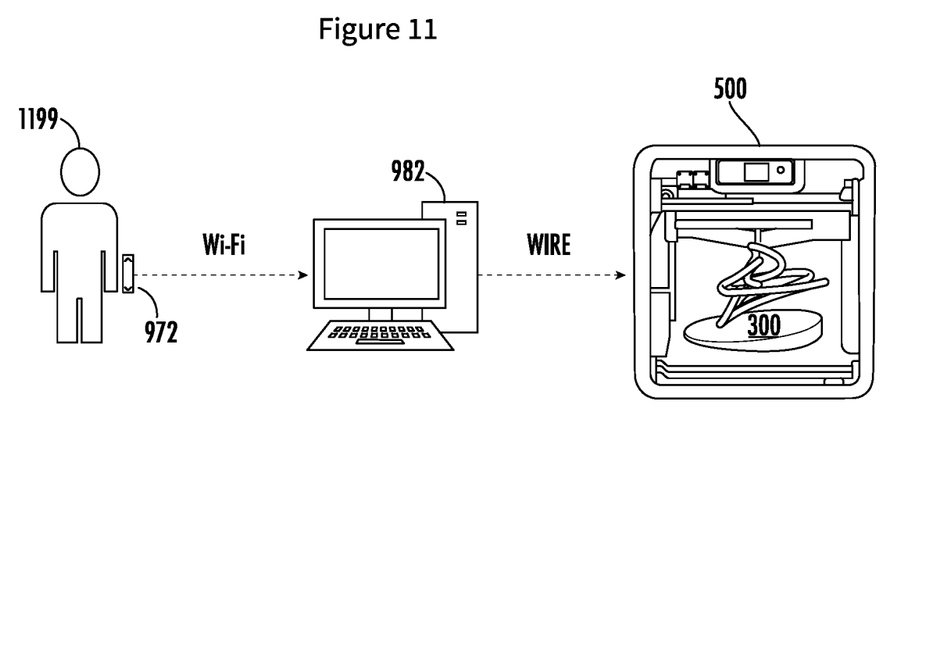
FIG. 11 presents a schematic diagram representing a system for fabricating a manufacture comprising a representation of a three dimensional plot of acceleration data according to certain embodiments of the present disclosure.

FIG. 11 presents a schematic diagram illustrating a system for fabricating a manufacture representing a three dimensional plot of acceleration data, according to certain embodiments of the present disclosure. A user (1199) carries an accelerometer device (972) which may be similar to that described in FIG. 9. The accelerometer device (972) wirelessly communicates unprocessed acceleration data to a computing device (982) using the Wi-Fi data protocol. The computing device (982) maps a virtual three dimensional plot of the acceleration data and converts it into instructions which control a three dimensional printer (500) to fabricate a manufacture (300) comprising a model representing a three dimensional plot of acceleration data as measured by the accelerometer device (972).

Figure 12:
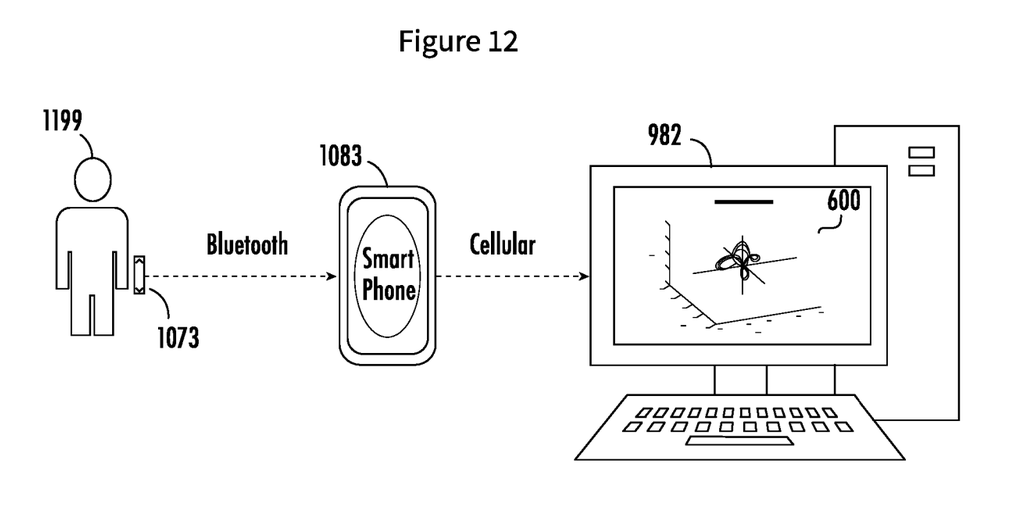
FIG. 12 presents a schematic diagram representing a system for rendering a three dimensional plot of acceleration data in two dimensions on a display monitor according to certain embodiments of the present disclosure.

FIG. 12 presents a schematic diagram illustrating a system for rendering a three dimensional plot of acceleration data on a display monitor, according to certain embodiments of the present disclosure. A user (1199) carries a motion monitor (1073) which may be similar to that described in FIG. 10. The motion monitor (1073) wirelessly communicates unprocessed acceleration data to a smart phone (1083) via the Bluetooth communication protocol. The smart phone (1083), in turn, transmits the acceleration data to a computing device (982) via cellular frequencies and protocols. The computing device (982) maps a virtual three dimensional plot of the acceleration data and applies programmed principles of perspective to render the virtual three dimensional model on a display monitor as a two dimensional image (600).

The above description is neither exclusive nor exhaustive and is intended neither to describe all possible embodiments (also called "examples") nor to limit the scope of the claims. Embodiments may include elements in addition to those in the described embodiments and, in some cases, may contain only a subset of the elements described in a particular embodiment. Embodiments may contain any combination of elements in the described embodiments in addition to elements not expressly described. As used herein, the articles "a" and "an" may include one or more than one of the noun modified by either without respect to other uses of phrases such as "one or more" or "at least one." The word "or" is used inclusively unless specified otherwise. Terms such as "first," "second," "third" and so forth are used as labels to distinguish elements and do not indicate sequential order unless otherwise indicated. In addition to the embodiments described above, embodiments of the invention include any that would fall within the scope of the Claims, below.

What is claimed is:

1. A method of rendering a three-dimensional acceleration plot of one or more steps on a graphical user interface, the method comprising:

receiving, by a computing device, outputs from an accelerometer that is configured to be coupled to an individual taking one or more steps while coupled to the accelerometer, and wherein each of the outputs correspond to a respective magnitude of acceleration along a respective one of three orthogonal axes at a plurality of time periods;

mapping, using the computing device, the outputs to a virtual three-dimensional acceleration plot of the outputs, the virtual three-dimensional acceleration plot comprising a plurality of points, wherein each point of the plurality of points is positioned according to coordinates proportional to the magnitudes of acceleration along the three orthogonal axes at a first time period of the plurality of time periods;

applying, by the computing device, automated techniques of visual perspective to the virtual three-dimensional acceleration plot to yield two or more virtual two-dimensional images of the virtual three-dimensional acceleration plot, each of the two or more virtual two-dimensional images showing respective multiple perspectives of the virtual three-dimensional acceleration plot to create the impression that the virtual three-dimensional acceleration plot is changing orientation in relation to at least one of the three orthogonal axes; and rendering, by the computing device, the two or more virtual two-dimensional images on a graphic output device in an animated sequence, wherein each of the two or more virtual two-dimensional images are rendered on the graphic output device at different times.

2. The method of claim 1 in which the each point of the plurality of points:

except for a first sequential point of the plurality of points, is visually coupled to a second point, the second point positioned according to coordinates proportional to the magnitudes of acceleration along the three orthogonal axes at a second time period of the plurality of time periods, the second time period occurring before the first time period of the plurality of time periods; and except for a final sequential point of the plurality of points, is visually coupled to a third point, the third point positioned according to coordinates proportional to magnitudes of acceleration along the three orthogonal axes at a third time period, the third time period occurring after the first time period.

3. The method of claim 2 in which the first sequential point is visually coupled to the final sequential point.

4. The method of claim 2 in which:
the first sequential point is positioned according to coordinates proportional to the magnitudes of acceleration along the three orthogonal axes at a first sequential time period;
the first sequential time period occurs during a first instance of a reference foot of the individual contacting a ground;
the final sequential point is positioned according to coordinates proportional to the magnitudes of acceleration along the three orthogonal axes at a final sequential time period; and
the final sequential time period occurs during a second instance of the reference foot of the individual contacting the ground.

5. The method of claim 2 in which the one or more steps comprise multiple strides and:
the first time period is a first relative time within a gait cycle;
the magnitudes of acceleration along the three orthogonal axes at the first time period are aggregate measures of acceleration at two or more instances of the first relative time;
the second time period is a second relative time within the gait cycle;
the magnitudes of acceleration along the three orthogonal axes at the second time period are aggregate measures of acceleration at two or more instances of the second relative time;
the third time period is a third relative time within the gait cycle; and
the magnitudes of acceleration along the three orthogonal axes at the third time period are aggregate measures of acceleration at two or more instances of the third relative time.

6. The method of claim 1 in which at least one of the three orthogonal axes is determined relative to a direction of gravitational pull.

7. A system for rendering a three-dimensional acceleration plot of one or more steps on a graphical user interface, the system comprising at least one processor and at least one memory storing instructions that, with the at least one processor, cause the system to:
receive outputs from an accelerometer that is configured to be coupled to an individual taking one or more steps while coupled to the accelerometer, wherein each of the outputs correspond to a respective magnitude of acceleration along a respective one of three orthogonal axes at a plurality of time periods;
map the outputs to a virtual three-dimensional acceleration plot, the virtual three-dimensional acceleration plot comprising a plurality of points, wherein each point of the plurality of points is positioned according to coordinates proportional to the magnitudes of acceleration along the three orthogonal axes at a first time period of the plurality of time periods;
apply automated techniques of visual perspective to the virtual three-dimensional acceleration plot to yield two or more virtual two-dimensional images of the virtual three-dimensional acceleration plot, each of the two or more virtual two-dimensional images showing respective multiple perspectives of the virtual three-dimensional acceleration plot to create the impression that the virtual three-dimensional acceleration plot is changing orientation in relation to at least one of the three orthogonal axes; and
render the two or more virtual two-dimensional images on a graphic output device in an animated sequence, wherein each of the two or more virtual two-dimensional images are rendered on the graphic output device at different times.

8. The system of claim 7 in which each point of the plurality of points:
except for a first sequential point of the plurality of points, is visually coupled to a second point, the second point positioned according to coordinates proportional to magnitudes of acceleration along the three orthogonal axes at a second time period, the second time period occurring before the first time period; and
except for a final sequential point of the plurality of points, is visually coupled to a third point, the third point positioned according to coordinates proportional to magnitudes of acceleration along the three orthogonal axes at a third time period, the third time period occurring after the first time period.

9. The system of claim 8 in which:
the first sequential point is positioned according to coordinates proportional to the magnitudes of acceleration along the three orthogonal axes at a first sequential time period;
the first sequential time period occurs during a first instance of a reference foot of the individual contacting a ground;
the final sequential point is positioned according to coordinates proportional to the magnitudes of acceleration along the three orthogonal axes at a final sequential time period; and
the final sequential time period occurs during a second instance of the reference foot of the individual contacting the ground.

10. The system of claim 8 in which the one or more steps comprise multiple strides and:
the first time period is a first relative time within a gait cycle;
the magnitudes of acceleration along the three orthogonal axes at the first time period are aggregate measures of acceleration at two or more instances of the first relative time;
the second time period is a second relative time within the gait cycle;
the magnitudes of acceleration along the three orthogonal axes at the second time period are aggregate measures of acceleration at two or more instances of the second relative time;
the third time period is a third relative time within the gait cycle; and
the magnitudes of acceleration along the three orthogonal axes at the third time period are aggregate measures of acceleration at two or more instances of the third relative time.

11. The system of claim 7 in which the plurality of time periods are measured using one or more of: the outputs generated by the accelerometer; a time cycle of the at least one processor in a computing device; a quartz clock; an electric clock; or a radio-controlled clock, the radio-controlled clock being wirelessly synchronized with an atomic clock.

12. The system of claim 7, powered by one or more of: a lithium ion battery; a nickel metal hydride battery; a photovoltaic cell; a body heat ambient energy collector; or a body motion ambient energy collector.

13. A graphical user interface (GUI) for rendering a three-dimensional acceleration plot of one or more steps on a two-dimensional medium, wherein the GUI:
   displays two or more images of the three-dimensional acceleration plot in two dimensions on a graphic output device using automated techniques of visual perspective in an animated sequence, the three-dimensional acceleration plot comprising a plurality of points,
   wherein each of the two or more images of the three-dimensional acceleration plot in two dimensions show different perspectives of the three-dimensional acceleration plot and are displayed by the GUI at different times,
   wherein each point of the plurality of points is positioned according to coordinates proportional to magnitudes of acceleration along three orthogonal axes at a first time period of a plurality of time periods,
   wherein the magnitudes of acceleration are based at least in part on outputs received from an accelerometer that is configured to be coupled to an individual while the individual takes one or more steps, and
   wherein each of the outputs correspond to a respective magnitude of acceleration along a respective one of three orthogonal axes at the plurality of time periods.

14. The GUI of claim 13 in which each point of the plurality of points:
   except for a first sequential point of the plurality of points, is visually coupled to a second point, the second point positioned according to coordinates proportional to the magnitudes of acceleration along the three orthogonal axes at a respective second time period, the second time period occurring before the first time period; and
   except for a final sequential point of the plurality of points, is visually coupled to a third point, the third point positioned according to coordinates proportional to the magnitudes of acceleration along the three orthogonal axes at a third time period, the third time period occurring after the first time period.

15. The GUI of claim 14 in which the first sequential point is coupled to the final sequential point.

16. The GUI of claim 14 in which:
   the first sequential point is positioned according to coordinates proportional to the magnitudes of acceleration along the three orthogonal axes at a first sequential time period;
   the first sequential time period occurs during a first instance of a reference foot of the individual contacting a ground;
   the final sequential point is positioned according to coordinates proportional to the magnitudes of acceleration along the three orthogonal axes at a final sequential time period; and
   the final sequential time period occurs during a second instance of the reference foot of the individual contacting the ground.

17. The GUI of claim 14 in which the one or more steps comprise multiple strides and:
   the first time period is a first relative time within a gait cycle;
   the magnitudes of acceleration along the three orthogonal axes at the first time period are aggregate measures of acceleration at two or more instances of the first relative time;
   the second time period is a second relative time within the gait cycle;
   the magnitudes of acceleration along the three orthogonal axes at the second time period are aggregate measures of acceleration at two or more instances of the second relative time;
   the third time period is a third relative time within the gait cycle; and
   the magnitudes of acceleration along the three orthogonal axes at the third time period are aggregate measures of acceleration at two or more instances of the third relative time.

18. The GUI of claim 13 in which at least one of the three orthogonal axes is an adjusted axis.

* * * * *

UNITED STATES PATENT AND TRADEMARK OFFICE
CERTIFICATE OF CORRECTION

PATENT NO. : 11,607,850 B2
APPLICATION NO. : 16/250196
DATED : March 21, 2023
INVENTOR(S) : Sara Ehlert Taylor It is certified that error appears in the above-identified patent and that said Letters Patent is hereby corrected as shown below:

In the Claims

In Column 12, Line 57, Claim 2, delete "which the" and insert -- which --, therefor.

In Column 15, Line 35, Claim 14, delete "a respective" and insert -- a --, therefor.

Signed and Sealed this
Sixth Day of June, 2023

Katherine Kelly Vidal
*Director of the United States Patent and Trademark Office*